United States Patent
Tuo et al.

(10) Patent No.: US 10,161,862 B2
(45) Date of Patent: Dec. 25, 2018

(54) METHOD FOR ANALYZING MOLECULAR WEIGHT OF THE POLY-P-PHENYLENE TEREPHTHALAMIDE

(71) Applicants: SHANDONG WANSHENGBO SCI-TECH.CO., LTD., Donying, Shandong (CN); TSINGHUA UNIVERSITY, Beijing (CN)

(72) Inventors: Xinlin Tuo, Beijing (CN); Qinghai Cui, Dongying (CN)

(73) Assignees: SHNGDONG WANSHENGBO SCI-TECH.CO., LTD., Dongying, Shangdong (CN); TSINGHUA UNIVERSITY, Beijing (CN)

( * ) Notice: Subject to any disclaimer, the term of this patent is extended or adjusted under 35 U.S.C. 154(b) by 77 days.

(21) Appl. No.: 15/318,667

(22) PCT Filed: Apr. 7, 2016

(86) PCT No.: PCT/CN2016/078631
§ 371 (c)(1),
(2) Date: Dec. 13, 2016

(87) PCT Pub. No.: WO2017/156805
PCT Pub. Date: Sep. 21, 2017

(65) Prior Publication Data
US 2018/0128737 A1    May 10, 2018

(30) Foreign Application Priority Data
Mar. 15, 2016    (CN) .......................... 2016 1 0147338

(51) Int. Cl.
*D01F 6/60*    (2006.01)
*C08G 69/32*    (2006.01)
(Continued)

(52) U.S. Cl.
CPC .......... *G01N 21/359* (2013.01); *C08G 69/32* (2013.01); *G01N 11/02* (2013.01); *G01N 33/442* (2013.01);
(Continued)

(58) Field of Classification Search
CPC .. G01N 21/359; G01N 21/3563; G01N 11/02; G01N 2021/3572; G01N 2011/008; C08G 69/32
See application file for complete search history.

(56) References Cited

U.S. PATENT DOCUMENTS

| 2002/0082383 A1* | 6/2002 | Kurose | ................. C08G 69/04 528/332 |
| 2005/0017399 A1* | 1/2005 | Otto | ......................... C08J 5/06 264/184 |
| 2009/0246435 A1* | 10/2009 | Shimono | .................. B32B 1/08 428/36.91 |

OTHER PUBLICATIONS

Gou et al. "Reaction Mechanism of Terephthaloyl Chloride/-Methyl-2-pyrrolidone and the Effect on Poly( -phenylene terephthalamide) Polymerization", Chinese Journal of Organic Chemistry, vol. 34, No. 3, Jun. 30, 2014.*

* cited by examiner

Primary Examiner — Dominic J Bologna
(74) Attorney, Agent, or Firm — Raymond Y. Chan; David and Raymond Patent Firm

(57) ABSTRACT

A method for analyzing molecular weight of the poly-p-phenylene terephthalamide (PPTA) utilizing near infrared spectrum is provided for reducing the time required to analyze the molecular weight of PPTA. The method uses PPTA samples to build a spectrum-viscosity fitting curve. The molecular weight of an unknown PPTA is analyzed via a near infrared analysis software and the spectrum-viscosity (Continued)

fitting curve. The method is beneficial in that it has a short process time and high reliability.

1 Claim, 2 Drawing Sheets

(51) Int. Cl.
*D01F 13/04* (2006.01)
*D01D 5/38* (2006.01)
*D01D 10/06* (2006.01)
*D01F 1/10* (2006.01)
*D01F 11/08* (2006.01)
*G01N 21/359* (2014.01)
*G01N 11/02* (2006.01)
*G01N 33/44* (2006.01)
*G01N 21/3563* (2014.01)
*G01N 11/00* (2006.01)

(52) U.S. Cl.
CPC .... *G01N 21/3563* (2013.01); *G01N 2011/008* (2013.01); *G01N 2021/3572* (2013.01)

METHOD FOR ANALYZING MOLECULAR WEIGHT OF THE POLY-P-PHENYLENE TEREPHTHALAMIDE

CROSS REFERENCE OF RELATED APPLICATION

This is the National Stage of and claims priority to international application number PCT/CN2016/078631, international filing date Apr. 7, 2016, the entire contents of each of which are expressly incorporated herein by reference.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a method for analyzing molecular weight, and more particularly to a method for analyzing the molecular weight of poly (p-phenylene terephthalamide) (PPTA) utilizing near infrared spectrum.

Description of Related Arts

Para-aramid fiber is a new material that possesses excellent properties including high thermal stability, solvent resistance, high strength, high modulus, and light weight. This material is used in many high tech applications, especially important in civil and defense applications. Maintaining a stable molecular weight in the para-aramid fiber is key in the production process of the material. Currently, detecting the molecular weight of the material at the same time of poly (p-phenylene terephthalamide) (PPTA) production is a difficult technical problem.

PPTA is a rigid liquid crystal composite. It is insoluble in ordinary solvent except strong acid such as concentrated sulfuric acid, nitric acid, and chlorine sulfonic acid. Thus, it is impossible to analyze the molecular weight of PPTA using gel permeation chromatography. Currently, the method to analyze the molecular weight of PPTA is based on concentrated sulfuric acid. First, the PPTA is slowly dissolved into concentrated sulfuric acid. Then, an Ubbelohde viscometer is used to measure the time of this process. An instrinsic viscosity is obtained by comparing the time with the concentration of sulfuric acid, which is then used to analyze the molecular weight of PPTA. This method, however, is time consuming, as it requires a lot of time to dissolve the PPTA into concentrated sulfuric acid. For example, it needs more than 48 hours to dissolve PPTA in 98% concentrated sulfuric acid to yield viscosity between 6.0 to 6.5 dL/g. Scientists have attempted to speed up the dissolve time by adding other chemicals, such as alkali (NaH KOH), which reduced the dissolve time to approximately 5 hours, and N-Methyl pyrrolidone, which reduced the dissolve time to approximately 3 hours. Still, the dissolve time is too long for monitoring in real-time.

SUMMARY OF THE PRESENT INVENTION

The present invention features a new method for analyzing the molecular weight of poly (p-phenylene terephthalamide) (PPTA) utilizing near infrared spectrum. The invention is advantageous in that it provides a method for reducing the time required to analyze the molecular weight of PPTA, which utilizes near infrared spectrum. The method utilizes a computer to analyze the molecular weight of PPTA in a real-time system by calculating the minor differences between before and after polymerization of near infrared electron transition from N—H bonds to amino.

Accordingly, the present invention utilizes near infrared spectroscopy that includes frequency doubling and combination band of molecular vibration spectrum such as Hydrogen containing group (O—H N—H C—H). Characteristics information of the Hydrogen containing group can be obtained from the near infrared spectrum. Particularly in the case of PPTA, only C—H and N—H are present in the molecules. In the case of C—H, polymerization would be slightly affected; but in the case of N—H, polymerization would have an obvious effect as it transitions from —NH2 to —CONH—. Thus, it is possible to analyze the molecular weight by utilizing near infrared spectrum.

Additionally, the analysis of the near infrared spectroscopy requires numerous samples uniformly distributed on a detection range to build a regression model. Thus, many samples with different viscosity are applied to ensure the degree of accuracy of the model. A viscosity value between 5 to 7 dL/g is considered acceptable, with 6 to 6.5 dL/g being exceptional.

Another advantage of the invention is to provide a method for analyzing the molecular weight of poly (p-phenylene terephthalamide) (PPTA) utilizing near infrared spectrum, wherein the method has a low cost, short process time, simple control structure, high reliability, and good practicability without destroying the samples.

Another advantage of the invention is to provide a method for analyzing the molecular weight of poly (p-phenylene terephthalamide) (PPTA) utilizing near infrared spectrum, wherein the method does not require additional chemical reagents.

Another advantage of the invention is to provide a method for analyzing the molecular weight of poly (p-phenylene terephthalamide) (PPTA) utilizing near infrared spectrum, wherein the method does not comprise harmful pollution to the environment.

Another advantage of the invention is to provide a method for analyzing the molecular weight of poly (p-phenylene terephthalamide) (PPTA) utilizing near infrared spectrum, wherein the method results in measurement that has good tradeoff between detection speed and accuracy.

Another advantage of the invention is to provide a method for analyzing the molecular weight of poly (p-phenylene terephthalamide) (PPTA) utilizing near infrared spectrum, wherein the method can be implemented to centralize analysis and control of a production process.

Additional advantages and features of the invention will become apparent from the description which follows, and may be realized by means of the instrumentalities and combinations particular point out in the appended claims.

According to the present invention, the foregoing and other objects and advantages are attained by a method for analyzing the molecular weight of poly (p-phenylene terephthalamide) (PPTA) utilizing near infrared spectrum, comprising the following steps:

(a) choosing at least 60 PPTA samples with viscosity ranging from 1 to 9 dL/g to build a fitting curve;

(b) dissolving PPTA samples in concentrated sulfuric acid and detecting the viscosity by an Ubbelohde viscometer;

(c) using a near infrared spectrometer to scan the PPTA samples at least 6 times to obtain an average spectrum;

(d) extrapolating a spectrum-viscosity fitting curve from the viscosity data of step (b) and the spectrum of the step (c) via a near infrared analysis software; and (e) using the near infrared spectrometer to scan an unknown PPTA resin to obtain a near infrared spectrum and calculating the viscosity of the unknown PPTA by the spectrum-viscosity fitting curve.

It is worth mentioning that the PPTA viscosity data are inputted into a near infrared spectrum analysis software in order to link the viscosity data to the spectrum, wherein the near infrared spectrum analysis software will conclude a regression model.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
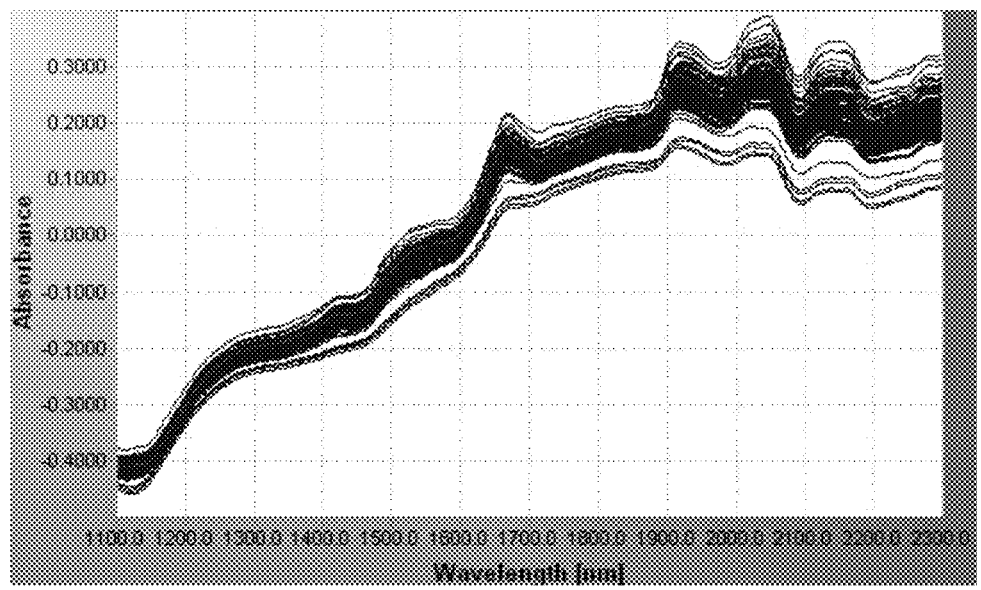
FIG. 1 is a graph illustrating the raw data of PPTA near infrared spectrum.
Figure 2:
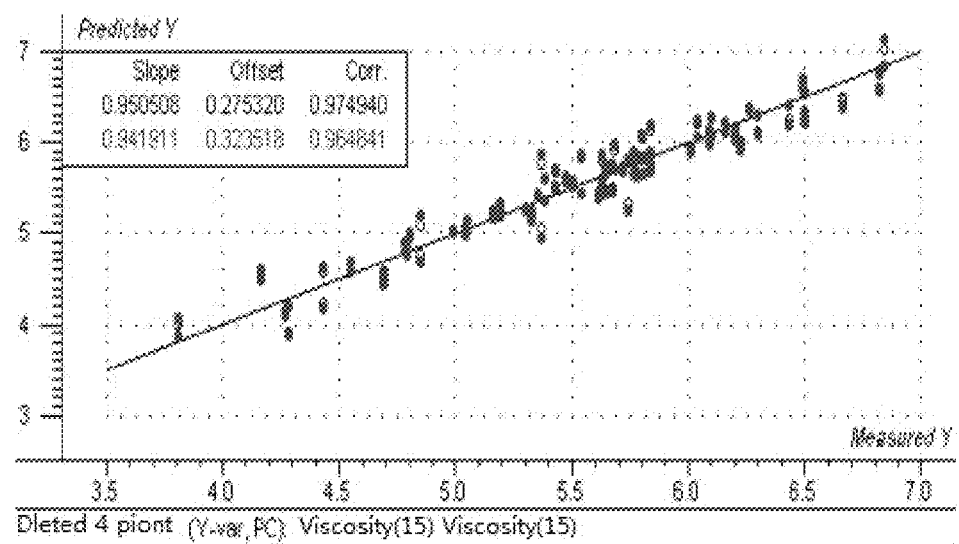
FIG. 2 is a graph of a contrast diagram, illustrating the presumable results based on the PPTA spectrum-weight regression equation (spot) and real results based on the Ubbelohde viscometer (circle).
Figure 3:
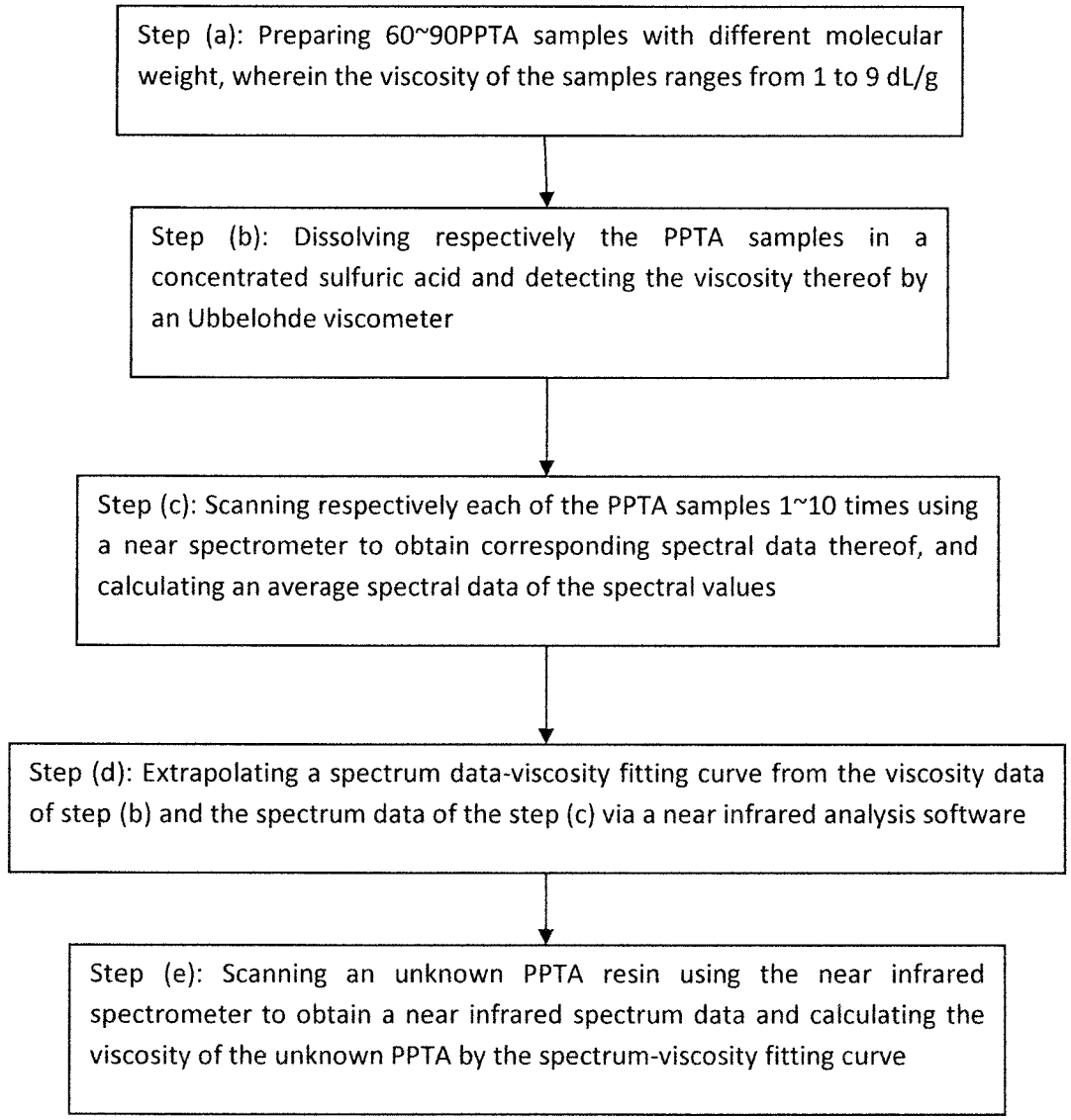
FIG. 3 is the flow chart of the claimed method to detect the molecular weight utilizing the near infrared spectrum.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

According to a first preferred embodiment of the present invention, a method for analyzing molecular weight of poly (p-phenylene terephthalamide) (PPTA) utilizing near infrared spectrum comprises the steps of:

(a) choosing approximately 60 PPTA samples with viscosity ranging from 1 to 9 dL/g to build a fitting curve;

(b) dissolving PPTA samples in concentrated sulfuric acid and detecting the viscosity by an Ubbelohde viscometer;

(c) using a near infrared spectrometer to scan the PPTA samples 6 times to obtain an average spectrum;

(d) extrapolating a spectrum-viscosity fitting curve from the viscosity data of step (b) and the spectrum of the step (c) via a near infrared analysis software; and (e) Using the near infrared spectrometer to scan an unknown PPTA resin to obtain a near infrared spectrum and calculating the viscosity of the unknown PPTA by the spectrum-viscosity fitting curve.

It is worth mentioning that in the step (c), the model of the near infrared spectrometer is Luminar 5030; and in the step (d), the near infrared analysis software is SNAP 2.03.

It is also worth mentioning that the method for analyzing molecular weight of poly (p-phenylene terephthalamide) (PPTA) can be implemented as an ongoing analysis process for a manufacturing line.

According to a second embodiment of the present invention, a method for analyzing molecular weight of poly (p-phenylene terephthalamide) (PPTA) utilizing near infrared spectrum comprises the steps of:

(a) choosing approximately 90 PPTA samples with viscosity ranging from 1 to 9 dL/g to build a fitting curve;

(b) dissolving PPTA samples in concentrated sulfuric acid and detecting the viscosity by an Ubbelohde viscometer;

(c) using a near infrared spectrometer to scan the PPTA samples 10 times to obtain an average spectrum;

(d) extrapolating a spectrum-viscosity fitting curve from the viscosity data of step (b) and the spectrum of step (c) via a near infrared analysis software; and (e) using the near infrared spectrometer to scan an unknown PPTA resin to obtain a near infrared spectrum and calculating the viscosity of the unknown PPTA by the spectrum-viscosity fitting curve.

According to a third embodiment of the present invention, a method for analyzing molecular weight of poly (p-phenylene terephthalamide) (PPTA) utilizing near infrared spectrum comprises the steps of:

(a) choosing approximately 70 PPTA samples with viscosity ranging from 1 to 9 dL/g to build a fitting curve;

(b) dissolving PPTA samples in concentrated sulfuric acid and detecting the viscosity by an Ubbelohde viscometer;

(c) using a near infrared spectrometer to scan the PPTA samples 7 times to obtain an average spectrum;

(d) extrapolating a spectrum-viscosity fitting curve from the viscosity data of step (b) and the spectrum of step (c) via a near infrared analysis software; and (e) using the near infrared spectrometer to scan an unknown PPTA resin to obtain a near infrared spectrum and calculating the viscosity of the unknown PPTA by the spectrum-viscosity fitting curve.

According to a fourth embodiment of the present invention, a method for analyzing molecular weight of poly (p-phenylene terephthalamide) (PPTA) utilizing near infrared spectrum comprises the steps of:

(a) choosing approximately 80 PPTA samples with viscosity ranging from 1 to 9 dL/g to build a fitting curve;

(b) dissolving PPTA samples in concentrated sulfuric acid and detecting the viscosity by an Ubbelohde viscometer;

(c) using a near infrared spectrometer to scan the PPTA samples 8 times to obtain an average spectrum;

(d) extrapolating a spectrum-viscosity fitting curve from the viscosity data of step (b) and the spectrum of step (c) via a near infrared analysis software; and (e) using the near infrared spectrometer to scan an unknown PPTA resin to obtain a near infrared spectrum and calculating the viscosity of the unknown PPTA by the spectrum-viscosity fitting curve.

The viscosity of four unknown PPTA groups calculated by said method of the first preferred embodiment of present invention and sulphuric acid viscosity was compared, and the specific as shown as the following table:

| No. | NIR viscosity | H2SO4 viscosity | Relative deviation % |
| --- | --- | --- | --- |
| 1 | 3.94 | 3.81 | 3.35 |
| 2 | 4.83 | 4.79 | 0.73 |
| 3 | 5.94 | 5.8 | 2.37 |
| 4 | 6.92 | 6.84 | 1.18 |
| Relative deviation % | | 1.91 | |

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purpose of illustrating the functional and structural principles of the present invention and is subject to change without departure from such principles. Therefore, this invention includes all modifications encompassed within the spirit and scope of the following claims.

What is claimed is:

1. A method for analyzing molecular weight of the poly-p-phenylene terephthalamide (PPTA) utilizing near infrared spectrum, comprising the following steps:
   (a) preparing 60~90PPTA samples with different molecular weight, wherein the viscosity of said PPTA samples ranges from 1 to 9 dL/g;
   (b) dissolving respectively said PPTA samples in a concentrated sulfuric acid and detecting the viscosity thereof by an Ubbelohde viscometer;
   (c) scanning respectively each of said PPTA samples 1~10 times using a near infrared spectrometer to obtain corresponding spectral data thereof, and calculating an average spectral data of said spectral values;
   (d) extrapolating a spectrum data-viscosity fitting curve from said viscosity data of step (b) and said spectrum data of the step (c) via a near infrared analysis software; and
   (e) scanning an unknown PPTA resin using said near infrared spectrometer to obtain a near infrared spectrum data and calculating the viscosity of said unknown PPTA by said spectrum-viscosity fitting curve.

* * * * *

UNITED STATES PATENT AND TRADEMARK OFFICE
CERTIFICATE OF CORRECTION

PATENT NO. : 10,161,862 B2  
APPLICATION NO. : 15/318667  
DATED : December 25, 2018  
INVENTOR(S) : Xinlin Tuo and Qinghai Cui Page 1 of 1

It is certified that error appears in the above-identified patent and that said Letters Patent is hereby corrected as shown below:

On the Title Page

The Name of the first Applicant: "SHANGDONG WANSHENGBOSCI-TECH.CO." should be read - AFCHINA CORPORATION CO., LTD -.
The Name of the first Assignee: "SHANGDONG WANSHENGBOSCI-TECH.CO." should be read - AFCHINA CORPORATION CO., LTD -.

Signed and Sealed this
Twenty-sixth Day of February, 2019

Andrei Iancu
*Director of the United States Patent and Trademark Office*